United States Patent [19]

Lee

[11] Patent Number: 4,539,430

[45] Date of Patent: Sep. 3, 1985

[54] PREPARATION OF ETHYLENEDIAMINE DINITRATE

[75] Inventor: Kien-yin Lee, Los Alamos, N. Mex.

[73] Assignee: The United States of America as represented by the United States Department of Energy, Washington, D.C.

[21] Appl. No.: 611,558

[22] Filed: May 17, 1984

[51] Int. Cl.$^3$ .............................................. C07C 87/14
[52] U.S. Cl. .................................. 564/511; 564/512; 260/688; 149/92; 149/111
[58] Field of Search ............... 564/511, 512, 438, 437; 260/688; 149/92, 111

[56] References Cited

U.S. PATENT DOCUMENTS

| | | | |
|---|---|---|---|
| 2,385,128 | 9/1945 | Castner | 260/688 |
| 3,711,552 | 1/1973 | Foster et al. | 260/688 |
| 4,236,014 | 11/1980 | Lee et al. | 548/267 |
| 4,339,618 | 7/1982 | Rosner | 260/688 |
| 4,353,758 | 10/1982 | Akst et al. | 149/92 |

OTHER PUBLICATIONS

Akst et al., "Explosive Performance Modification by Cosolidification of Ammonium Nitrate with Fuels" 10/76 Picatinny Arsenal.

*Primary Examiner*—Charles F. Warren
*Assistant Examiner*—Harry B. Shubin
*Attorney, Agent, or Firm*—Samuel M. Freund; Paul D. Gaetjens; Judson R. Hightower

[57] ABSTRACT

Method for the preparation of ethylenediamine dinitrate. Ethylenediamine dinitrate, a useful explosive, may readily be prepared by solvent extraction of nitrate ion from an acidic aqueous solution thereof using a high-molecular-weight, water-insoluble amine dissolved in an organic solvent, and reacting the resulting organic solution with ethylenediamine. The process of the instant invention avoids the use of concentrated nitric acid, as is currently practiced, resulting in a synthesis which is far less hazardous especially for large quantities of the explosive, and more efficient.

7 Claims, No Drawings

4,539,430

PREPARATION OF ETHYLENEDIAMINE DINITRATE

This invention is the result of a contract with the Department of Energy (Contract No. W-7405-ENG-36).

BACKGROUND OF THE INVENTION

The present invention relates generally to the preparation of ethylenediamine dinitrate, and more particularly to a method for the safe and economical preparation of ethylenediamine dinitrate in an organic medium without the use of concentrated nitric acid and using water-insoluble amines as a vehicle for achieving the dissolution of the starting materials.

Ethylenediamine dinitrate is a chemical explosive which finds use as a component in pressed mixtures for shells and as a component in castable eutectic mixtures with ammonium nitrate and other compounds for bomb fills. It is currently prepared according to a process described in "Explosive Performance Modification by Cosolidification of Ammonium Nitrate with Fuels," by I. Akst and J. Hershkowitz, Technical Report 4987 from the Picatinny Arsenal, Dover, N.J. (1976). Therein the authors teach the preparation of ethylenediamine dinitrate in batches of 50 to 500 grams by acidifying a cooled solution of ethylenediamine, water and ethanol with concentrated nitric acid, stirring for some period of time, filtering the precipitated ethylenediamine dinitrate product, and washing and drying the precipitate. This method is inefficient, because of the necessity of the use of concentrated nitric acid for the reaction.

The use of high-molecular-weight, water-insoluble amines as vehicles for rendering ionic organic compounds soluble in organic solvents is well-known. In "Production of the Ammonium Salt of 3,5-dinitro-1,2,4-triazole by Solvent Extraction," U.S. Pat. No. 4,236,014 issued to Kien-yin Lee and Donald G. Ott on Nov. 25, 1980, the inventors describe the use of a high-molecular-weight, water-insoluble amine to extract a large organic acid starting material from aqueous solution into solution with an organic solvent, from where a chemical reaction is made to occur with other compounds producing thereby an ionic organic product which is insoluble in the organic solvent. The method of the subject invention, however, includes the extraction of an inorganic acid from aqueous solution using a high-molecular-weight, water-insoluble amine, rendering it soluble in an organic solvent thereby, from which the chemical reaction which leads to the desired insoluble ethylenediamine dinitrate product can be performed safely and efficiently. Of significant unobvious nature in this type of extraction is whether the amine extracting agent will be released by the base used as one of the principal reactants in the desired synthesis. That is, it is desirable that the amine be released in its original form after the addition reaction of the organic base which leads to the production of the desired product. It is not possible to predict whether ethylenediamine is basic enough to displace the amine in the acid nitrate salt of the amine extracting agent, which replacement is essential to the success of the subject invention.

SUMMARY OF THE INVENTION

Accordingly, it is an object of the present invention to provide a method for the preparation of ethylenediamine dinitrate.

Another object of the subject invention is to provide a safer method for the preparation of ethylenediamine dinitrate.

Yet another object of my invention is to permit the use of waste acidic solutions of nitrate ions to prepare usable ethylenediamine dinitrate.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the method of this invention may comprise forming an aqueous phase which includes nitrate ions in an acidic environment, forming a liquid organic phase which includes at least one water-insoluble amine capable of extracting nitric acid from aqueous solution, contacting the liquid organic phase and the aqueous phase for a time period sufficient to achieve substantial extraction of the nitrate ions by the water-insoluble amine producing thereby a nitrate salt of the amine which is soluble in the liquid organic phase, separating the aqueous phase which is depleted in nitrate ions and an equivalent of hydrogen ions from the liquid organic phase, contacting the organic liquid containing the nitrate salt of the water-insoluble amine with ethylenediamine for a sufficient length of time for substantial chemical reaction to occur, whereby the desired ethylenediamine dinitrate is produced, and separating the ethylenediamine dinitrate from the liquid organic phase. It is preferred that the water-insoluble amines employed be of high-molecular-weight and further be aliphatic secondary or tertiary amines. It is also preferred that the aqueous solution be a nitric acid solution. Preferably, the liquid organic phase includes a water-insoluble organic diluent in which the water-insoluble aliphatic amine or amines, the nitrate salt or salts thereof, and ethylenediamine are very soluble, while the desire ethylenediamine dinitrate is substantially insoluble therein and precipitates readily therefrom. Preferably also, the water-insoluble aliphatic amine or amines include trilauryl amine. It is also preferred that the organic diluent include 1,2-dichloroethane. Preferably, the liquid organic phase containing the nitrate salt of the amine is dried after being separated from the depleted aqueous phase before being contacted with the ethylenediamine, whereby substantially all traces of moisture are removed, thereby improving the yield of ethylenediamine dinitrate.

The subject invention then is a method for the preparation of ethylenediamine dinitrate. The instant method avoids the danger inefficiency of the use of concentrated nitric acid, and permits the use of waste solutions of nitric acid for the neutralization process as a result of the amine extraction step which removes the nitrate from aqueous solution and places it in a form better suited for the safe and efficient reaction with the ethylenediamine.

DETAILED DESCRIPTION OF THE INVENTION

The subject invention is directed to a method for preparing ethylenediamine dinitrate by carrying out the addition reaction of ethylenediamine in organic solution thereby avoiding the use of concentrated nitric acid which both decreases the risk of explosion during the preparation, and increases the overall efficiency of the synthesis. In its broad aspect, the method of the instant invention encompasses the preparation of other coordination compounds of ethylenediamine. For example, ethylenediamine diperchlorate $((CH_2NH_2)_2—2HClO_4)$ and ethylenediamine dichlorate $((CH_2NH_2)_2—2HClO_3)$, both of which are explosives, can be prepared.

Production of ethylenediamine dinitrate in accordance with the process of the instant invention relies on the extraction of nitrate ion from an acidic aqueous solution by use of a high-molecular-weight, water-insoluble secondary or tertiary aliphatic amine dissolved in a water-insoluble organic solvent, followed by reaction of the resulting salt of the extracting amine or amines with ethylenediamine to form the desired product. The extraction by the aliphatic amine of the nitrate ions from the acidic aqueous solution in which they are prepared is achieved by ion-pair formation of the nitrate ions and an equivalent of hydrogen ions with an equivalent of aliphatic amine dissolved in the water-insoluble organic solvent according to the following reaction:

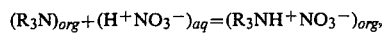

$$(R_3N)_{org} + (H^+NO_3^-)_{aq} = (R_3NH^+NO_3^-)_{org},$$

where $R_3N$ is high-molecular-weight tertiary aliphatic amine, and the subscripts "org" and "aq" indicate organic and aqueous phases, respectively. By replacing one of the "R" groups with hydrogen, secondary amines may be utilized. As best understood by the inventor, the ion-pair salts of only secondary and tertiary aliphatic amines have sufficient solubility in organic solvents to permit the reaction with ethylenediamine to occur with substantial efficiency. The "R" groups may be straight- or branched-chain alkyl groups in accordance with the present invention. The aqueous phase may include any acidic solution containing nitrate ion, but aqueous nitric acid solution is preferred. The nitric acid solution might contain impurities and could actually be a waste nitric acid solution. The synthesis is completed by the reaction of the aliphatic amine salt with ethylenediamine which is sufficiently basic to release the aliphatic amine from the ion-pair salt to its original form. It is essential that the aliphatic amine be chosen such that the ethylenediamine can regenerate the amine in its free base form according to the reaction:

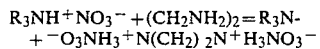

$$R_3NH^+NO_3^- + (CH_2NH_2)_2 = R_3N + {}^-O_3NH_3^+N(CH_2)_2N^+H_3NO_3^-$$

from which the aliphatic amine may readily be recycled and reused for the preparation of additional ethylenediamine dinitrate. It has been found that the efficiency of extraction is increased if the high-molecular-weight, water-insoluble aliphatic amine is diluted with an organic solvent which gives a substantially complete and rapid separation between the organic and aqueous phases. The water-insoluble organic solvent is further preferably chosen such that it can dissolve the ion-pair salt of the aliphatic amine and the ethylenediamine, while precipitating the ethylenediamine dinitrate product for ease of recovery of this material.

Reference will now be made in detail to the present preferred embodiment of the invention which is illustrated in the accompanying example.

EXAMPLE

Turning now to the example, the process of the instant invention commences with the formation of an aqueous phase containing nitrate ion in an acidic environment. Preferably, this aqueous phase is a nitric acid solution. Trilauryl tertiary amine is diluted with 1,2-dichloroethane, which is a water-immiscible hydrocarbon solvent, forming an organic phase. On a bench scale, the organic phase and the nitric acid solution are then mixed in a separatory funnel. After shaking the mixture well for a time period sufficient to ensure adequate contact time for the extraction of a significant quantity of the nitric acid from the aqueous phase by the tertiary amine, thereby bringing the nitrate ions into the organic phase, the mixture is allowed to settle, in order for the organic phase to separate from the depleted aqueous phase. The organic phase is then removed from contact with the aqueous phase and dried using magnesium sulfate or anhydrous ammonium sulfate to remove substantially all traces of water. After filtering, a stoichiometric quantity of ethylenediamine is added dropwise to the stirred filtrate. Preferably, the organic solution is cooled to between about 0° and −4° C. before the addition of the ethylenediamine. The white solid precipitate resulting therefrom is collected by filtration and washed several times with 1,2-dichloroethane. The solid is then dried under vacuum or by flowing air. The filtrate from the final filtration contains the regenerated trilauryl amine which may be reused after being washed with water and dried using a drying agent.

There are several commercially available, water-insoluble amines which are useful as anion exchangers and may be used in the practice of the instant invention. Trilauryl amine is sold under the Trade Name Alamine 304 by General Mills Chemicals, Inc. In Alamine 336, from the same company, the alkyl groups are a $C_8$–$C_{10}$ mixture. Moreover, Amberlite LA-2, which is a secondary amine sold under this Trade Name by Rohm and Haas Company, has a molecular weight in the range between 353 and 395. It has one lauryl group, the other organic group being a branched alkyl group having about 13 carbon atoms. The three above-described high-molecular-weight, water-insoluble amines have been successfully used for the preparation of ethylenediamine dinitrate. However, the trilauryl amine gave the most satisfactory performance.

The foregoing description of the preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What I claim is:

1. A method for the preparation of ethylenediamine dinitrate which comprises the steps of:

a. forming an aqueous phase which includes nitrate ions in an acidic environment;
b. forming a liquid organic phase which includes at least one water-insoluble amine capable of extracting nitric acid from aqueous solution;
c. contacting said liquid organic phase with said aqueous phase for a time period sufficient to achieve significant extraction of said nitrate ions in an acidic environment by said water-insoluble amine producing thereby a nitrate salt of said amine, said salt being soluble in said liquid organic phase;
d. separating said aqueous phase from said liquid organic phase containing said nitrate salt of said amine, said aqueous phase being depleted in nitrate ions and an equivalent of hydrogen ions;
e. contacting said liquid organic phase containing said nitrate salt of said amine with ethylenediamine for a sufficient time period for substantial chemical reaction to occur, whereby ethylenediamine dinitrate is produced, the liquid organic phase becoming depleted in said nitrate salt of said amine; and
f. separating the ethylenediamine dinitrate from said liquid organic phase.

2. The method as described in claim 1, wherein said at least one water-insoluble amine includes an aliphatic tertiary amine.

3. The method as described in claim 2, wherein said aqueous phase includes a solution of nitric acid.

4. The method as described in claim 3, wherein said liquid organic phase includes a water-insoluble organic diluent in which said water-insoluble aliphatic tertiary amine, said nitrate salt of said insoluble aliphatic tertiary amine and said ethylenediamine are very soluble, and wherein the ethylenediamine dinitrate is substantially insoluble.

5. The method as described in claim 4, wherein said water-insoluble aliphatic tertiary amine includes trilauryl amine.

6. The method as described in claim 5, wherein said organic diluent includes 1,2-dichloroethane.

7. The method as described in claim 6, wherein said liquid organic phase containing said nitrate salt of said amine is dried after being separated from said depleted aqueous phase and before being contacted with said ethylenediamine, whereby substantially all water is removed from said liquid organic phase.

* * * * *